United States Patent [19]

Domány et al.

[11] Patent Number: 5,155,123
[45] Date of Patent: Oct. 13, 1992

[54] PYRIDINE DERIVATIVES AND PHARMACEUTICAL COMPOSITIONS CONTAINING THEM

[75] Inventors: György Domány; Elemér Ezer; István Schon; Judit Matuz; Katalin Sághy; Lászlo Szporny; György Hajós; Márta Rényei, all of Budapest, Hungary

[73] Assignee: Richter Gedeon Vegyeszeti Gyar R.T., Budapest, Hungary

[21] Appl. No.: 607,153

[22] Filed: Oct. 31, 1990

[30] Foreign Application Priority Data

Nov. 7, 1989 [HU] Hungary .................. 5807/89

[51] Int. Cl.⁵ .................. A61K 31/44; C07D 213/74
[52] U.S. Cl. ...................... 514/353; 546/306
[58] Field of Search .................. 546/306; 514/353

[56] References Cited

FOREIGN PATENT DOCUMENTS 0009362 4/1980 European Pat. Off. .
0259738 3/1988 European Pat. Off. .

OTHER PUBLICATIONS

Chemical Abstracts, Abstract No. 7429r, vol. 111, No. 1, p. 715, Jul. 3, 1989.
Brewster et al., Organic Chemistry, 3rd Edition, pp. 494-498.
Chem. Abstracts, 70:37615a (1969).
Chem. Abstracts, 111:97258m (1989).
J. Med. Chem., vol. 14, No. 10, pp. 988-990 (1971).
Gastroenterology, vol. 5, pp. 43-61 (1945).
J. Am. Chem. Soc., 77, pp. 3154-3155 (1955).
Chem. Ber. 88 IVO. 7 1103 (1955).
Derwent Abstract 89-011891/02 which is equivalent to Chem. Abstract 111:7429r, (1989), cited by Examiner as (G) above.
Derwent Abstract 89-011891/02 which is equivalent to Chem. Abstracts 111:97258m.

Primary Examiner—Alan L. Rotman
Assistant Examiner—James H. Turnipseed
Attorney, Agent, or Firm—Herbert Dubno; Jonathan Myers

[57] ABSTRACT

The invention relates to novel pyridine derivatives of formula (I),

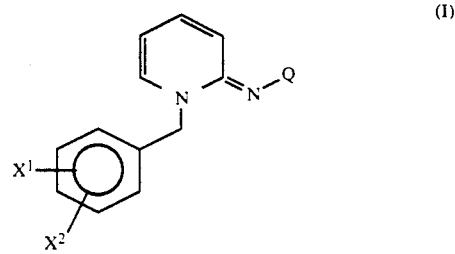

wherein
Q stand for a nitro or cyano group; and
$X^1$ and $X^2$, independently from each other, represent hydrogen or halogen or a trifluoromethyl, a lower alkyl or alkoxy or nitro group bound to any of the carbon atoms of the phenyl ring.

The invention further relates to pharmaceutical compositions containing these compounds and a process for their preparation.

The compounds of formula (I) possess gastric acid secretion inhibiting, tissue-protecting, analgetic and mild antiinflammatory effects and are useful for therapeutical purposes.

8 Claims, No Drawings

PYRIDINE DERIVATIVES AND PHARMACEUTICAL COMPOSITIONS CONTAINING THEM

FIELD OF THE INVENTION

The invention relates to the novel, therapeutically active pyridine derivatives of formula (I),

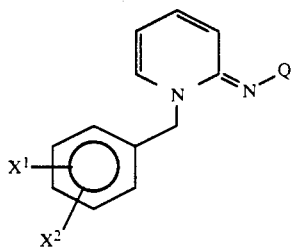

wherein

Q stands for a nitro or cyano group; and $X^1$ and $X^2$, independently from ech other, represent hydrogen or halogen or a trifluoromethyl, a lower alkyl or alkoxy or nitro group bound to any of the carbon atoms of the phenyl ring. The invention also relates to the preparation of such compound and to pharmaceutical compositions containing these compounds.

The compounds of formula (I), i.e. the compounds according to the invention possess important biological actions. The most important of these are inhibition of gastric acid secretion and tissue-protecting effect. Several representatives of these novel compounds exert also analgesic and mild antiinflammatory effects.

The invention also relates to a process for the preparation of the above compounds and of compositions containing one or more pyridine derivative of formula (I), as well as to a method of treatment. This method comprises administering a therapeutically effective amount of a compound of formula (I) to a patient for inhibiting the gastric acid secretion, for protecting tissues, for relieving pain or for treating a mild inflammation.

As used herein "lower" relates to an alkyl group or the alkyl moiety of an alkoxy group or an open-chain compound containing a short carbon chain consisting of at most 8 carbon atoms.

BACKGROUND OF THE INVENTION

The biological activity of a few compounds which are structurally similar to the compounds of the present invention is known. E.g. the alkylation on the ring nitrogen of 2-(nitroamino)pyridine with α-haloketones, α-haloesters and phenylethyl halides has been described in: J. Med. Chem. 14, 988 (1971). The antiinflammatory effect of the compounds obtained has also been described therein.

In the European patent specification No. 9,362 (1980) guanidine-type compounds have been described. A subgroup of these compounds consists of (1-methyl-2-pyridylidene)guanidine derivatives. The substances described in this specification possess hypoglycemic, secretion-inhibiting and cardiovascular activities.

Among the insecticidal compounds described in the published Japanese patent applications Nos. 63,307,857 (1988) and 63,287,764 (1988) as well as in the published European patent application No. 0,259,738 (1988) are 2-(cyanoimino)- and 2-(nitroimino)pyridines substituted on the ring nitrogen by a cyanoalkyl or 3-cyanobenzyl group or by a heterocyclic group through the methylene group.

DESCRIPTION OF THE INVENTION

The gastric acid secretion-inhibiting effect of the compounds according to the present invention was studied using Shay's method [Gastroenterology 5, pages 43 to 61 (1945)]. According to this method female H-Wistar rats weighing 120 to 150 g were starved in latticed cages for 24 hours. The animals received water ad libitum. Then their pylorus was ligated under a slight ether anaesthesia. The test compounds were administered during the surgical intervention. After 4 hours the animals were killed by ether narcosis. After excision of the stomach the volume and pH value of the gastric content were measured. In several cases the hydrochloric acid content was determined by titration.

The $ED_{50}$ values (given as mg/kg) determined in the above test are as follows:

|  | $ED_{50}$ mg/kg |
| --- | --- |
| 1-(2-chlorobenzyl)-2-(cyanoimino)pyridine | 1.80 |
| 1-benzyl-2-(cyanoimino)pyridine | 3.26 |
| 2-(cyanoimino)-1-(2-fluorobenzyl)pyridine | 4.30 |
| 2-(cyanoimino)-1-(4-fluorobenzyl)pyridine | 8.36 |
| 1-(3-chlorobenzyl)-2-(cyanoimino)pyridine | 9.88 |
| 2-(cyanoimino)-1-(2-methylbenzyl)pyridine | 11.70 |
| 2-(cyanoimino)-1-(3-trifluoromethylbenzyl)pyridine | 12.20 |
| 1-benzyl-2-(nitroimino pyridine | 13.55 |

It is noted as a comparison that the oral $ED_{50}$ value of cimetidine (chemically 1-cyano-2-methyl-3-[2-[[(5-methylimidazol-4-yl)methyl]thio]ethyl]-guanidine) is 50 mg/kg in the above test.

An 50 mg/kg oral dose of 1-benzyl-2-(cyanoimino)-pyridine inhibits the development of gastric ulcers induced in rats by 40 mg/kg subcutaneous (s.c.) dose of indomethacine (chemically [1-(4-chlorobenzoyl)-2-methyl-5-methoxyindol-3-yl]acetic acid) by 100%.

No toxic symptom was induced in rats by a single oral dose of 120 mg/kg of the compound.

According to another aspect of the present invention, there is provided a process for the prepration of the pyridine derivatives of the formula (I), which comprises a) reacting a 2-(substituted amino)pyridine derivative of formula (III),

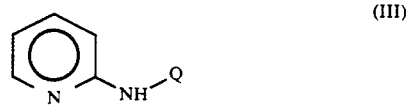

wherein Q is as defined above, with a benzyl halide of formula (IV),

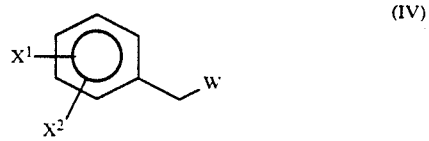

wherein $X^1$ and $X^2$ are as defined above and W means chlorine or bromine, in the presence of an organic or inorganic base, then separating the pyridine derivative of formula (I) obtained from the isomeric pyridine derivative of formula (V) formed as a by-product,

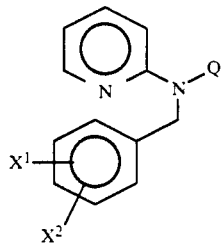

wherein, Q, $X^1$ and $X^2$ are as defined above; or b) reacting cyanogen bromide and a 2-iminopyridine derivative of the formula (II),

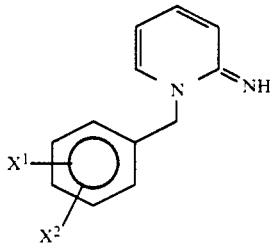

wherein $X^1$ and $X^2$ are as defined above, optionally prepared in situ by the alkaline treatment of a pyridinium salt of the formula (VI),

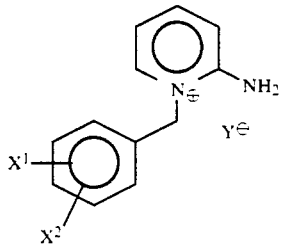

wherein $X^1$ and $X^2$ are as defined above and Y means halide ion, to obtain pyridine derivatives of formula (I) wherein $X^1$ and $X^2$ are as defined above and Q represents a cyano group.

The reaction according to the process a) is preferably carried out in a protic or dipolar aprotic solvent. Preferable solvents include lower alkanols such as ethanol; lower ketones such as acetone or lower alkanenitriles such as acetonitrile.

In process b) the 2-iminopyridine derivative of formula (II) used as starting material is suitably prepared in situ by treating an appropriately substituted 2-aminopyridinium salt of formula (VI) with a base. If the reaction with cyanogen bromide is carried out in the presence of an organic base as acid binding agent, 1 mole of cyanogen bromide should be used for 1 mole of the 2-iminopyridine derivative of formula (II). However, if this reaction is performed without any acid binding agent, only 0.5 mole of cyanogen bromide can be employed for 1 mole of the 2-iminopyridine derivative of formula (II). This reaction is preferably carried out in an ether-type solvent.

SPECIFIC EXAMPLES

The invention is illustrated in detail by the aid of the following non-limiting Examples.

EXAMPLE 1

Preparation of 1-benzyl-2-(nitroimino)pyridine 20 ml (0.114 mole) of N,N-diisopropylethylamine and 12 ml (0.1 mole) of benzyl bromide are added to a suspension containing 14 g (0.1 mole) of 2-(nitroamino)-pyridine [prepared according to J. Am. Chem. Soc. 77, 3154 (1955)] in 100 ml of acetonitrile, then the mixture is refluxed for 2.5 hours. The reaction mixture is cooled down then evaporated under reduced pressure, the residue is triturated with water, the suspension obtained is filtered and washed with a great volume of water. The filter cake is thoroughly sucked, then suspended in 50 ml of petroleum ether, filtered and washed again with petroleum ether to give 14.2 g (62%) of the named product, m.p.: 125°–126° C. (recrystallized from ethyl acetate).

From the petroleum ether filtrate the isomeric by-product, i.e. N-benzyl-N-nitro-2-pyridylamine hydrochloride, m.p.: 115°–116° C. (recrystallized from ethyl acetate) can be obtained by column chromatography and salt formation with hydrochloric acid.

By using the above process the following derivatives can be prepared:

1-(2-fluorobenzyl)-2-(nitroimino)pyridine, m.p.: 165°–166° C. (from ethanol),
1-(2-chlorobenzyl)-2-(nitroimino)pyridine, m.p.: 185°–186° C. (from acetonitrile),
1-(4-chlorobenzyl)-2-(nitroimino)pyridine, m.p.: 164°–165° C. (from ethanol),
1-(4-bromobenzyl)-2-(nitroimino)pyridine, m.p.: 184°–185° C. (from acetonitrile) and
1-(4-nitrobenzyl)-2-(nitrroimino)pyridine, m.p.: 224°–225° C. (from acetonitrile).

EXAMPLE 2

Preparation of 1-benzyl-2-(cyanoimino)pyridine 20 ml (0.114 mole) of N,N-diisopropylethylamine and 12 ml (0.1 mole) of benzyl bromide are added to a suspension containing 12 g (0.1 mole) of 2-(cyanoamino)-pyridine [prepared according to Ann. Pharm. Fr. 26, 469 (1968)] in 100 ml of acetonitrile. The reaction mixture is refluxed for 4 hours, then cooled down and evaporated under reduced pressure. The residue is triturated with water, filtered and washed with a great volume of water. The filter cake is thoroughly sucked, then suspended in 30 ml of ether, filtered and washed again with ether to yield 11.0 g (52.6%) of the named compound, m.p.: 147°–148° C. (from ethanol).

The isomeric by-product i.e. N-benzyl-N-cyano-2-pyridylamine, m.p.: 65°–66° C. (from ethanol), may be obtained from the ethereal filtrate by purification with column chromatography.

By using the above process the following derivatives can be prepared:

2-(cyanoimino)-1-(2-fluorobenzyl)pyridine, m.p.: 157°–158° C. (from isopropanol),
1-(2-chlorobenzyl)-2-(cyanoimino)pyridine, m.p.: 167°–168° C. (from ethanol),
2-(cyanoimino)-1-(4-fluorobenzyl)pyridine, m.p.: 147°–148° C. (from isopropanol), 1-(4-chlorobenzyl)-2-(cyanoimino)pyridine, m.p.: 168°-170° C. (from isopropanol),
1-(4-bromobenzyl)-2-(cyanoimino)pyridine, m.p.: 168°-170° C. (from ethanol),
2-(cyanoimino)-1-(4-nitrobenzyl)pyridine, m.p.: 208°-210° C. (from ethanol),
2-(cyanoimino)-1-(2,6-dichlorobenzyl)pyridine, m.p.: 219°-220° C. (from ethanol),
2-(cyanoimino)-1-(2-nitrobenzyl)pyridine, m.p.: 197°-199° C. (from acetonitrile),
2-(cyanoimino)-1-(2-methylbenzyl)pyridine, m.p.: 152°-154° C. (from acetonitrile),
2-(cyanoimino)-1-(3-methoxybenzyl)pyridine, m.p.: 133°-135° C. (from methanol),
2-(cyanoimino)-1-(4-methylbenzyl)pyridine, m.p.: 173°-174° C. (from ethanol),
1-(3-chlorobenzyl)-2-(cyanoimino)pyridine, m.p.: 175°-176° C. (from methanol) and
2-(cyanoimino)-1-(3-trifluoromethylbenzyl)pyridine, m.p.: 144°-145° C. (from ethanol).

EXAMPLE 3

Preparation of 1-benzyl-2-(cyanoimino)pyridine 7 g (50 mmole) of potassium carbonate and 6.5 ml (55 mmole) of benzyl bromide are weighted to the suspension of 6 g (50 mmole) of 2-(cyanoamino)pyridine in 100 ml of acetone, then the reaction mixture is refluxed under vigorous stirring for 2.5 hours. After cooling the inorganic salt is filtered off and the acetone filtrate is evaporated under reduced pressure. The residue is triturated with 10 ml of ether, filtered and washed twice with 5 ml of ether each to obtain 5.55 g (53.1%) of the named compound, m.p.: 142° C.

EXAMPLE 4

Preparation of 1-benzyl-2-(cyanoimino)pyridine 5.3 g (20 mmole) of 2-amino-1-benzylpyridinium bromide [prepared according to Chem. Ber. 88, 1103 (1955)] are suspended in 20 ml of ether, then 20 ml of aqueous sodium hydroxide solution of 0.5 mole/liter concentration are added while stirring. After the dissolution of the solid phase the phases are separated and the aqueous phase is extracted with 20 ml of ether. The combined organic phase is dried over anhydrous sodium sulfate and evaporated to its half volume under reduced pressure. Then, a solution containing 1.1 g (10 mmole) of cyanogen bromide in 5 ml of ether is dropped to the ethereal solution at room temperature under stirring. After stirring for 30 minutes the crystalline precipitate is filtered, washed with ether and then with a great volume of water, then the product is dried in air to yield 0.91 g (44%) of the named product, m.p.: 139°-140° C. (after recrystallization from ethanol the melting point raises to 147°-148° C.). On the basis of its melting point, infrared spectrum and thin layer chromatography (TLC) characteristics, this product proved to be indentical to the target compound of Example 2.

EXAMPLE 5

Preparation of tablets of a weight of 100 mg containing 10 mg of active ingredient each 50.0 g of active ingredient is mixed together with 285.0 g lactose, 100.0 g of potato starch, 2.5 g of sodium dodecyl sulfate, 5.0 of polyvinylpyrrolidone (Kollidon-K 90 ®), 50.0 g of microcrystalline cellulose (Avicel ®) and 7.5 g of vegetable oil (Sterotex ®) and after wet granulation, the product obtained is compressed to tablets weighing 100 mg each. Each of the tablets contains 10 mg of active ingredient.

EXAMPLE 6

Preparation of dragées of a weight of 125 mg containing 10 mg of active ingredient each The tablets prepared as described above are coated in a known manner with a layer consisting of sugar and talc, then the dragées obtained are polished with a mixture of bee wax and carnauba wax.

EXAMPLE 7

Preparation of capsules containing 20 mg of active ingredient each 40.0 g of active ingredient, 12.0 g of sodium lauryl sulfate, 102.0 g of lactose, 102.0 g of potato starch, 2.4 g of magnesium stearate and 1.6 g of colloidal silicon dioxide are thoroughly mixed together and the mixture obtained is filled into hard gelatine capsules containing 20 mg of active ingredient each.

We claim:

1. A compound of the Formula (I)

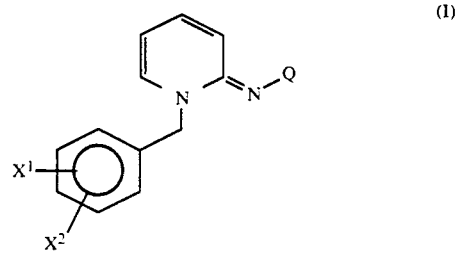

(I)

wherein

Q is a nitro or a cyano group; and $X^1$ and $X^2$, independently from each other, are hydrogen, halogen, trifluoromethyl, lower alkyl, lower alkoxy, or nitro bonded to any of the carbon atoms of the phenyl ring.

2. The compound of the Formula (I) defined in claim 1 and selected from the group consisting of:
1-benzyl-2-(nitroimino)pyridine,
1-(2-fluorobenzyl)-2-(nitroimino)pyridine,
1-(2-chlorobenzyl)-2-(nitroimino)pyridine,
1-(4-chlorobenzyl)-2-(nitroimino)pyridine,
1-(4-bromobenzyl)-2-(nitroimino)pyridine,
1-(4-nitrobenzyl)-2-(nitroimino)pyridine,
1-benzyl-2-(cyanoimino)pyridine,
2-(cyanoimino)-1-(2-fluorobenzyl)pyridine,
1-(2-chlorobenzyl)-2-(cyanoimino)pyridine,
1-(3-chlorobenzyl)-2-(cyanoimino)pyridine,
2-(cyanoimino)-1-(3-methoxybenzyl)pyridine,
2-(cyanoimino)-1-(3-trifluoromethylbenzyl)pyridine,
2-(cyanoimino)-1-(2-methylbenzyl)pyridine,
2-(cyanoimino)-1-(4-methylbenzyl)pyridine,
2-(cyanoimino)-1-(4-fluorobenzyl)pyridine,
1-(4-chlorobenzyl)-2-(cyanoimino)pyridine,
1-(4-bromobenzyl)-2-(cyanoimino)pyridine,
2-(cyanoimino)-1-(2-nitrobenzyl)pyridine,
2-(cyanoimino)-1-(4-nitrobenzyl)pyridine and
2-(cyanoimino)-1-(2,6-dichlorobenzyl)pyridine.

3. A compound of the Formula (I)

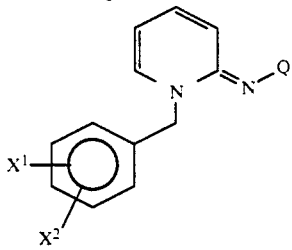

wherein

Q is a nitro or a cyano group; and $X^1$ and $X^2$, independently from each other, are hydrogen, halogen, trifluoromethyl, lower alkyl, or lower alkoxy bonded to any of the carbon atoms of the phenyl ring.

4. The compound of the Formula (I) defined in claim 3 and selected from the group consisting of:

1-(2-chlorobenzyl)-2-(cyanoimino)pyridine;
1-benzyl-2-(cyanoimino)pyridine;
2-(cyanoimino)-1-(2-fluorobenzyl)pyridine;
2-(cyanoimino)-1-(4-fluorobenzyl)pyridine;
1-(3-chlorobenzyl)-2-(cyanoimino)pyridine;
2-(cyanoimino)-1-(2-methylbenzyl)pyridine;
2-(cyanoimino)-1-(3-trifluoromethylbenzyl)pyridine; and
1-benzyl-2-(nitroimino)pyridine.

5. The compound of the Formula (I) defined in claim 3 which is 1-(2-chlorobenzyl)-2-(cyanoimino)-pyridine.

6. A pharmaceutical composition for the inhibition of gastric acid secretion which comprises a therapeutically effective amount of the compound of the Formula (I) defined in claim 1 together with a pharmaceutically acceptable inert carrier.

7. A pharmaceutical composition for the inhibition of gastric acid secretion which comprises a therapeutically effective amount of the compound of the Formula (I) defined in claim 3 together with a pharmaceutically acceptable inert carrier.

8. A method of inhibiting gastric acid secretion in a mammalian subject which comprises the step of administering to said mammalian subject a therapeutically effective amount of the compound of the Formula (I):

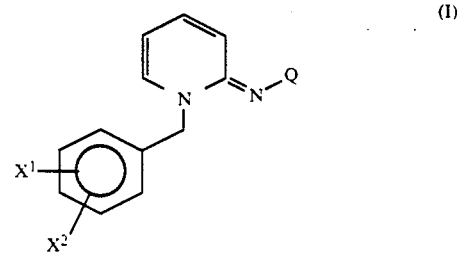

wherein

Q is a cyano or nitro group; and $X^1$ and $X^2$ independently from each other are each hydrogen, halogen, trifluoromethyl, or a lower alkyl, lower alkoxy. or nitro group bonded to any of the carbon atoms in the phenyl ring.

* * * * *